(12) United States Patent
Herbert

(10) Patent No.: US 6,942,774 B1
(45) Date of Patent: Sep. 13, 2005

(54) ELECTROPHORESIS APPARATUS AND A METHOD OF USING THE SAME

(75) Inventor: Ben Herbert, North Epping (AU)

(73) Assignee: Proteome Systems, Ltd., North Ryde (AU)

( * ) Notice: Subject to any disclaimer, the term of this patent is extended or adjusted under 35 U.S.C. 154(b) by 310 days.

(21) Appl. No.: 10/070,914

(22) PCT Filed: Sep. 8, 2000

(86) PCT No.: PCT/AU00/01065

§ 371 (c)(1),
(2), (4) Date: Mar. 8, 2002

(87) PCT Pub. No.: WO01/20315

PCT Pub. Date: Mar. 22, 2001

(30) Foreign Application Priority Data

Sep. 10, 1999 (AU) ............................................ PQ2760

(51) Int. Cl.[7] ................... G01N 27/447; G01N 27/453; B01D 57/02
(52) U.S. Cl. ....................... 204/456; 204/459; 204/465; 204/606; 204/610; 204/615; 204/616; 204/466; 204/666
(58) Field of Search ................... 204/456, 459, 204/465, 606, 610, 615, 616, 466, 666

(56) References Cited

U.S. PATENT DOCUMENTS

| 4,151,065 A | * | 4/1979 | Kaplan et al. ............... 204/620 |
| 4,391,688 A | * | 7/1983 | Hamelin ....................... 204/461 |
| 4,415,418 A | * | 11/1983 | Turre et al. .................. 204/466 |
| 4,443,319 A | | 4/1984 | Chait et al. |
| 4,666,581 A | * | 5/1987 | Itoh et al. .................... 204/616 |
| 5,275,710 A | | 1/1994 | Gombocz et al. |
| 5,785,835 A | | 7/1998 | Saito et al. |
| 6,558,522 B1 | * | 5/2003 | Williams et al. ............. 204/459 |
| 2002/0100690 A1 | * | 8/2002 | Herbert ....................... 204/610 |
| 2003/0015426 A1 | * | 1/2003 | Rooney et al. ............. 204/467 |
| 2003/0221962 A1 | * | 12/2003 | Ingenhoven et al. ........ 204/465 |
| 2004/0045829 A1 | * | 3/2004 | Ingenhoven et al. ........ 204/465 |

FOREIGN PATENT DOCUMENTS

| EP | 0 684 468 | 5/1995 | |
| WO | WO 98/57161 | 12/1998 | |
| WO | WO 98/57162 | 12/1998 | |
| WO | WO 99/33550 | 7/1999 | |
| WO | WO 9933550 A1 * | 7/1999 | ........... B01D/57/02 |

* cited by examiner

*Primary Examiner*—Alan Diamond
(74) *Attorney, Agent, or Firm*—Knobbe Martens Olson & Bear

(57) ABSTRACT

An apparatus for rehydrating and for performing electrophoresis on a gel strip includes a tray defining a plurality of parallel troughs configured to receive gel strips. Each trough defines a centrally located rehydration area and an electrode area disposed either side of the electrode area. End walls delimit the rehydration area of the trough from the electrode area. Electrode means including contact points adapted to contact either the gel strip in the electrode areas near the first and second end of the gel or a conducting or current carrying electrode bridge material which is in contact with the gel strip in the electrode areas. The electrode means are adapted to be connected to a means for supplying an electric current for imposing an electric potential in the strip between the electrodes.

23 Claims, 7 Drawing Sheets

ELECTROPHORESIS APPARATUS AND A METHOD OF USING THE SAME

This invention relates to an electrophoresis apparatus and to a method of using the same for separating biomolecules by electrophoresis.

BACKGROUND OF THE INVENTION

Two-dimensional electrophoresis is the preferred method for separating proteins from complex mixtures such as tissue samples, bacteria or plant material. Typically the proteins are separated in the first dimension using an electrophoresis gel with an immobilised pH gradient (IPG). These gels are commercially available and are usually supplied as dry gel strips bonded to a plastic backing sheet. Before the separation takes place the gel must be rehydrated with an appropriate liquid, in which it is ideal to have the protein sample dissolved. The most common embodiment of this approach is to allow the rehydration to occur passively, in a tray comprising a plurality of troughs, until the liquid in each trough has fully rehydrated the IPG gel strip in that trough. This requires that care is taken in selecting the correct volume of rehydration liquid to match the capacity of the IPG gel strip. If too little rehydration liquid is added the IPG will under-rehydrate and the separation will be compromised. Similarly, if too much rehydration liquid is added and some of that liquid is not taken up by the IPG gel strip then proteins are lost in the liquid which is not taken up into the gel. Typically, high molecular weight proteins are preferentially lost in this process.

To overcome this drawback with passive rehydration some groups have advocated the use of rehydration trays with electrodes embedded in the troughs. The electrodes are used to provide a voltage (~50 V) during the rehydration process. This electric field causes 'active' uptake of the proteins into the IPG gel matrix and results in more proteins entering the gel, especially high molecular weight proteins. However, if the rehydration solution comes in contact with both electrodes during the rehydration process, then the dissolved proteins may undergo electrophoretic transport to the electrodes in the free solution. If this occurs, a significant proportion of the proteins of the sample do not separate in the IPG because the sample proteins are transported to the electrode and then precipitate there. The proteins which are lost in this process represent all molecular weights, not only high molecular weight proteins.

The present invention aims to provide an IPG gel strip rehydration tray that allows active rehydration to be done without the free rehydration solution coming into contact with the electrodes, thus preventing the electrophoretic transport of the proteins to the electrodes.

DISCLOSURE OF INVENTION

In a first aspect of the present invention there is provided an apparatus for rehydrating and for performing electrophoresis on a gel strip including:
(a) a tray defining at least one trough configured to receive a gel strip, said trough defining a centrally located rehydration area and an electrode area disposed either side of the rehydration area;
(b) means for delimiting the rehydration area of the trough from the electrode area; and
(c) electrode means including contact points adapted to contact either the gel strip in the electrode areas near the first and second end of the gel or a conducting or current carrying electrode bridge material which is in contact with the gel strip in the electrode areas, the electrode means being adapted to be connected to a means for supplying an electric current for imposing an electric potential in the strip between the electrodes.

Existing apparatus for rehydrating IPG gel strips all have troughs with flat bases or floors. Indeed the provision of a flat floor in troughs for rehydrating IPG gel strips is taught as being necessary for satisfactory rehydration. In contrast the inventors of the present invention have realised that having a floor or base in which the dehydration area is delimited from the electrode area by for example having a stepped floor or a wall or both. In such a manner active rehydration can be carried out without the rehydration solution coming into contact with the electrodes, thus preventing the electrophoretic transport of the proteins to the electrodes in free solution. In a preferred embodiment a means of preventing the rehydration solution from contacting the electrodes include small walls extending across the width of the trough and a relatively small air gap between the electrodes and the walls.

In a further preferred embodiment the gel in the rehydration area of the trough contacts a conducting/current carrying, electrode bridge which completes the circuit to contact point of the electrodes.

The electrode bridges may comprise filter paper or the like wetted with an electrically conducting liquid.

It is preferred that the electrode area is deeper than the rehydration area.

Typically the tray will define a plurality of substantially parallel troughs.

The trays may be designed to allow electrodes to contact the gel/electrode bridge assembly from above, thus eliminating the need for embedded electrodes in the troughs.

This arrangement lends itself to a disposable IPG gel strip rehydration and running tray. The ability to use a disposable, combined IPG gel strip rehydration and running tray overcomes a number of drawbacks with other commercially available systems.

The trays may be supplied with the dry IPG gel strips and dry electrode bridge material already in place in the grooves, thus eliminating the major handling step of setting up the trays. In addition, with disposable trays there is no problem with carryover from one sample to the next, whereas the current commercial trays require careful washing between uses.

The electrode assembly may include moulded pressure points, which rest on the gel strip where it overlaps the electrode bridge to ensure a good electrical contact between the gel strip and the electrode bridge.

The invention also encompasses a method of rehydrating and performing electrophoresis on a gel strip using the apparatus according to the present invention and/or its preferred embodiments.

In a related aspect the invention provides a method of rehydrating and performing electrophoresis on a gel strip comprising the steps of:
(a) providing a tray defining at least one trough with a gel strip, located in said trough, the trough defining a centrally located rehydration area and an electrode area disposed either side of the electrode area in which an absorbent electrode bridge is provided, the trough including means for delimiting the rehydration area of the trough from the electrode area;
(b) wetting the bridges with an electrically conducting liquid;
(c) adding rehydration liquid, containing a sample to be separated by electrophoresis to the trough;

(d) inserting a dry gel strip into the trough if a gel strip is not already present in the trough, the gel strip being longer than the rehydration area so that its ends rest on the electrode bridges;

(e) applying relatively low voltage across the gel strip during a first period in which rehydration of the gel strip occurs;

(f) subsequently applying a relatively higher voltage to perform electrophoresis on the sample.

Typically the sample will be a mixture of macromolecules such as proteins, although other samples containing DNA, RNA, amino acids or other components which can be separated by electrophoresis may be used.

BRIEF DESCRIPTION OF THE DRAWINGS

The invention will now be described, by way of example only, and with reference to the accompanying drawings in which:—

DETAILED DESCRIPTION OF THE PRESENTLY PREFERRED EMBODIMENTS

Figure 1:
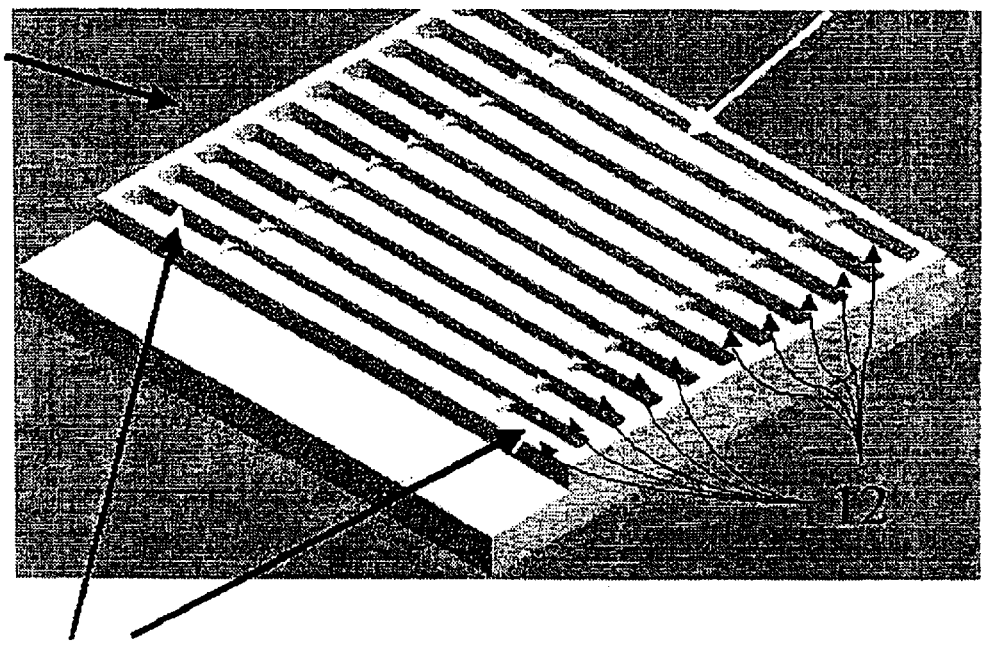
FIG. 1 is a schematic view of an apparatus for active rehydration of IPG gels.

Turning now to the drawings, FIG. 1 shows a first embodiment of an apparatus 10 for rehydrating dry IPG gels with the aid of an applied electric field. In the embodiment shown in FIG. 1 the tray has ten elongate parallel grooves or troughs 12. However the tray could have more or less than ten grooves. The grooves shown in FIG. 1 are 6 mm wide, however in other embodiments the grooves they may be relatively narrower or relatively wider than 6 mm.

Figure 2A:
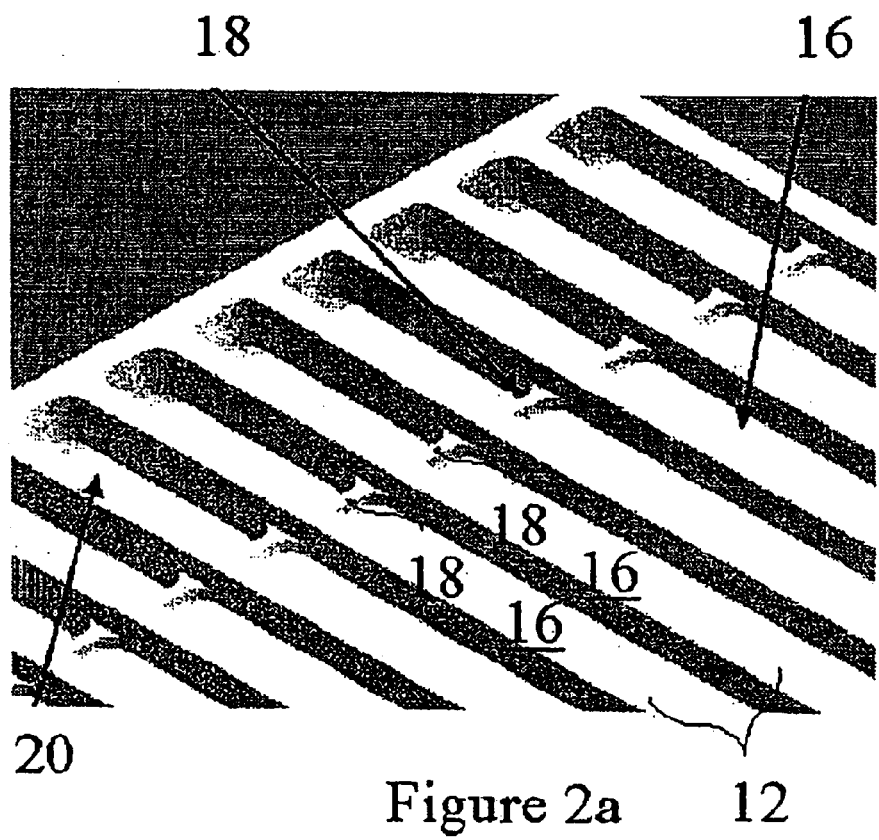
FIG. 2a shows an enlarged view of an electrode bridge area of the apparatus of FIG. 1.
Figure 2B:
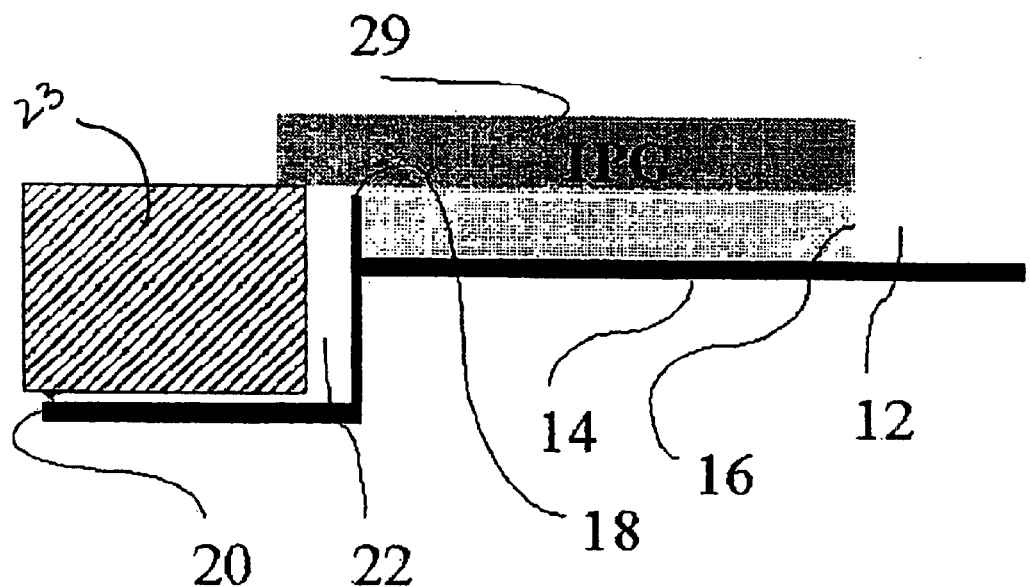
FIG. 2b is a schematic side view of walls which delimit a rehydration area of the apparatus.

FIG. 2a shows an expanded view of one end of the tray in FIG. 1 also shown schematically in FIG. 2b. Each groove 12 has a base or floor 14 which is stepped at each end. FIG. 2a shows only one end of each groove however both ends of each of the grooves are substantially identical. Each groove 12 defines a central rehydration area 16 at each longitudinal end of which there is a wall 18 which serves to contain the rehydration fluid within the designated rehydration area 18. The wall is about 1 mm above the floor of the rehydration area. There is an electrode bridge region 20 on the opposite side of each wall 18. The electrode bridge region is 1 mm below the floor of the rehydration area. The electrode bridge area may typically be 20 mm long and in use, as is discussed below, is sufficiently long to define an air gap 22 (FIG. 2b) between a piece of filter paper 23 or the like forming part of the bridge and the wall 18 which retains the rehydration solution. This prevents capillary movement from the rehydration area onto the electrode bridge region 20. The dimensions given above are however exemplary only and might be varied.

The grooves which are typically 6 mm wide allow room for loading the rehydration solution when an IPG gel strip is already in place in the groove, such as in the disposable tray format discussed above. Standard commercially available IPG gel strips are 3.3 mm wide, thus the 6 mm wide grooves will also allow for the use of relatively wider non-standard IPG gel strips up to approximately 5 mm wide.

The length of the grooves/trays may vary depending on the length of commercially available IPG gel strips which are to be used in the tray. Commercially available IPG gel strips are usually 7, 11, 13, 17 or 18 cm long.

The rehydration area may be approximately 5 mm shorter than the respective IPG gel strip to be rehydrated, to allow overlap of the IPG gel strip 29 (refer to FIG. 2b) into the electrode bridge area. The length of the electrode bridge area is 20 mm. In a preferred embodiment the electrode bridge area contains a 6 mm×20 mm piece of 2 mm thick filter paper 23 which fills the electrode bridge area except for a small air gap 22. A piece of filter paper that size requires between 50 and 200 $\mu$L of water to become slightly hydrated. The quantity of water in the electrode bridge area requires precise control, to allow electrical contact without excessive wetness, which would cause a disturbance in the separation.

In other embodiments of the design the electrode bridge area and/or the rehydration area could be scaled up or down in size to accommodate different requirements.

Figure 3:
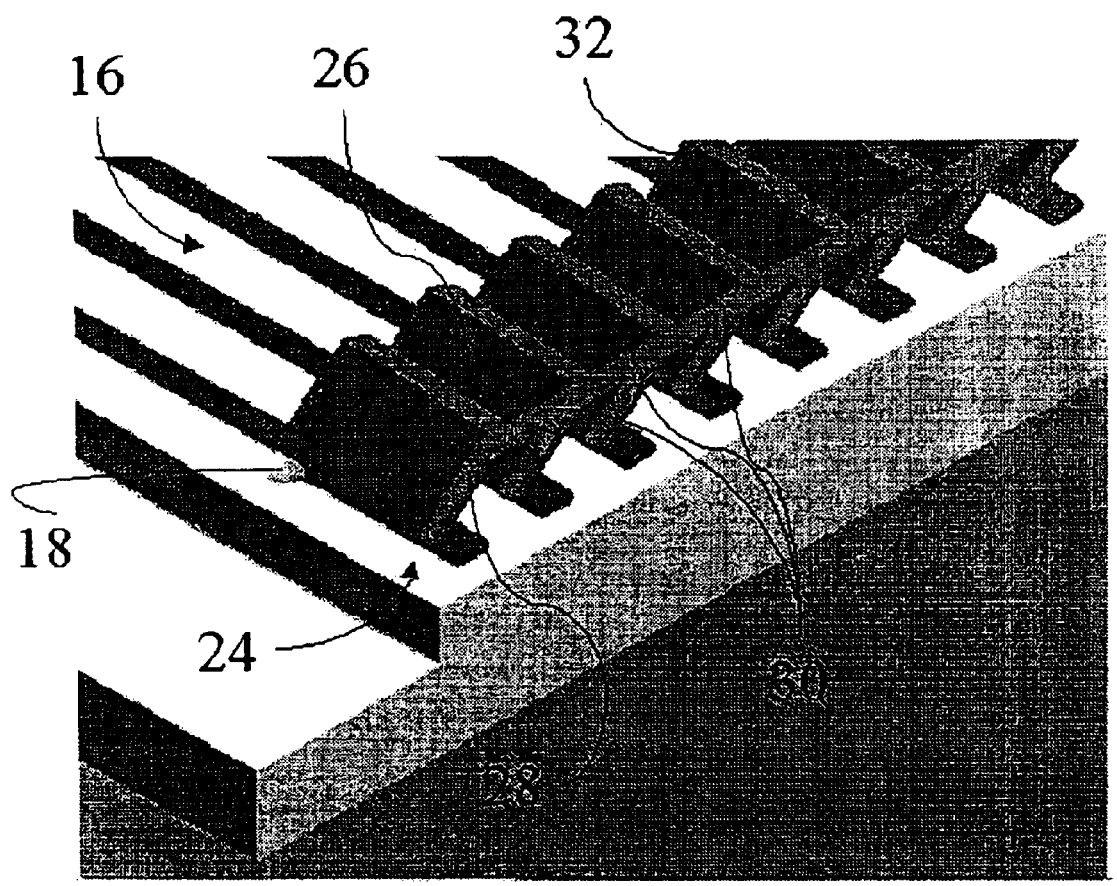
FIG. 3 illustrates an electrode assembly inserted into the electrode bridge area of the apparatus.

FIG. 3 shows an expanded view of one end of the tray in FIG. 1 illustrating an external electrode assembly 24 being lowered into the electrode bridge areas of the grooves.

The external electrode assembly 24 consists of a series of pressure blocks 26 (which are dark grey in FIG. 3) which rest/press on the IPG gel strip to ensure good contact between the IPG gel strip and the electrode bridge material and an electrode itself 28 (which is shown in light grey in FIG. 3). The electrode element comprises a series of electrode elements 30 located at the end of each pressure block which are integral with a joining element 32 linking the electrode elements together. The electrode elements are located near the outer edge of the trough to make full use of the length of the electrode bridge material.

The apparatus of the present invention allows for active loading of a rehydration liquid containing a biological sample to be separated into the gel strip for electrophoresis, ie loading while the current is running. Further it allows the use of filter paper or the like as an electrode bridge while the active loading is happening without getting the rehydration liquid onto the paper.

Figure 4A:
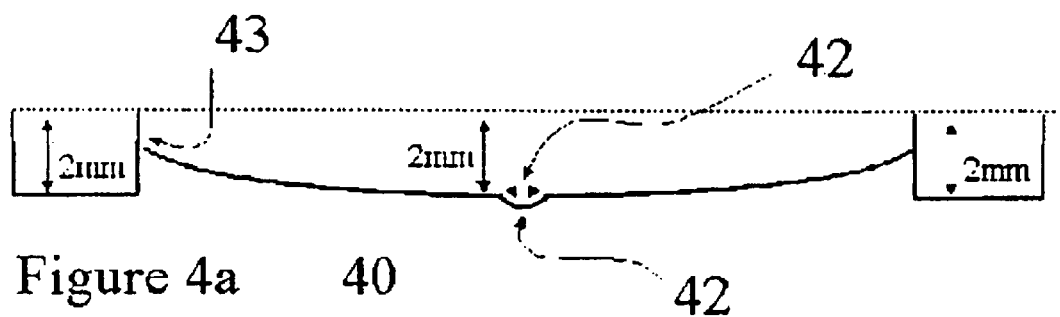
FIGS. 4 and 4a are schematic sectional views along the length of grooves of further embodiments of the invention.

FIG. 4a illusrates an alternative embodiment of the invention in which the base of the groove is curved along its length and in its centre, measured along the longitudinal direction or length of the groove defines a laterally extending loading channel 43 having a depth of 0.5 mm and a width w, measured in the longitudinal direction of the groove, of 2 mm. The curved base allows the maximum depth of the groove at its longitudinal centre to be 2 mm, so it can contain more rehydration liquid. The curved floor of the rehydration area supports the IPG strip well. The height h of the end walls 43 is 0.5 mm.

Figure 4B:
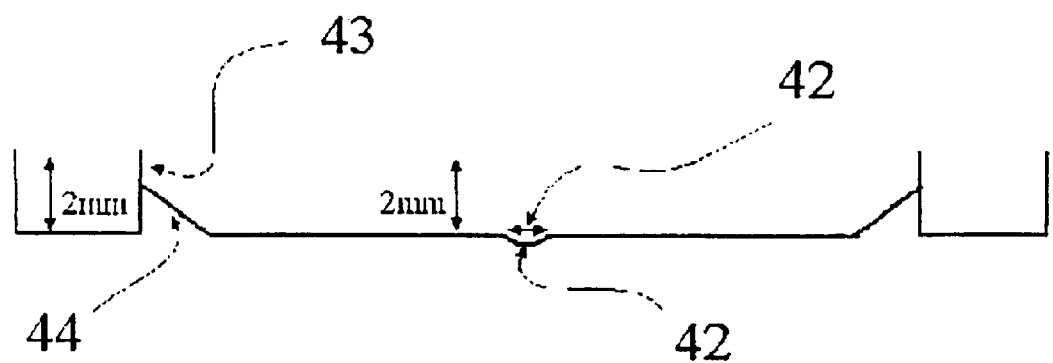

FIG. 4b shows a variant of the design of FIG. 4a in which the floor of the rehydration are is flat and there are two sloping end sections 44 at the ends of the rehydration are which slope at about 30 degrees. The channel 42 is identical to that of FIG. 4b.

Figure 5:
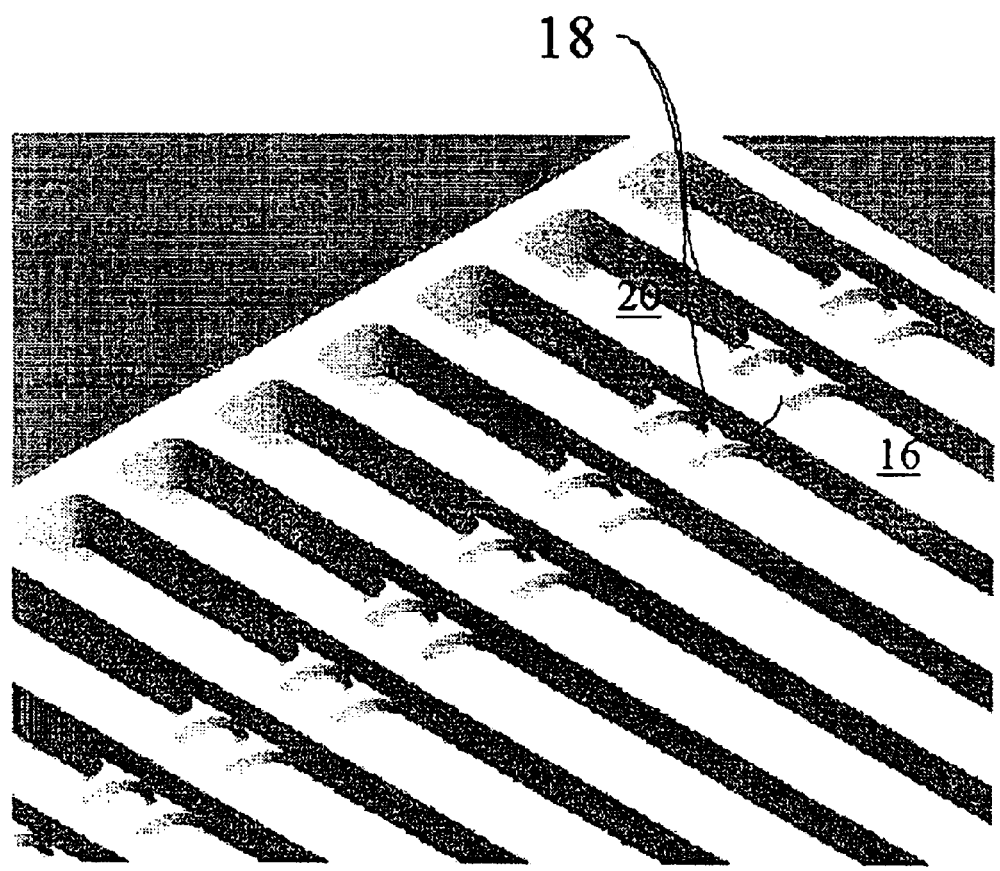
FIG. 5 is an isometric view of a yet further embodiment of the invention.

FIG. 5 illustrates a yet further variant of the invention in which two parallel walls 18 delimit the ends of the rehydration area 16 of the grooves. This helps to maintain an air gap between the rehydration solution and the electrode bridge area.

COMPARATIVE EXAMPLE

Figure 6:
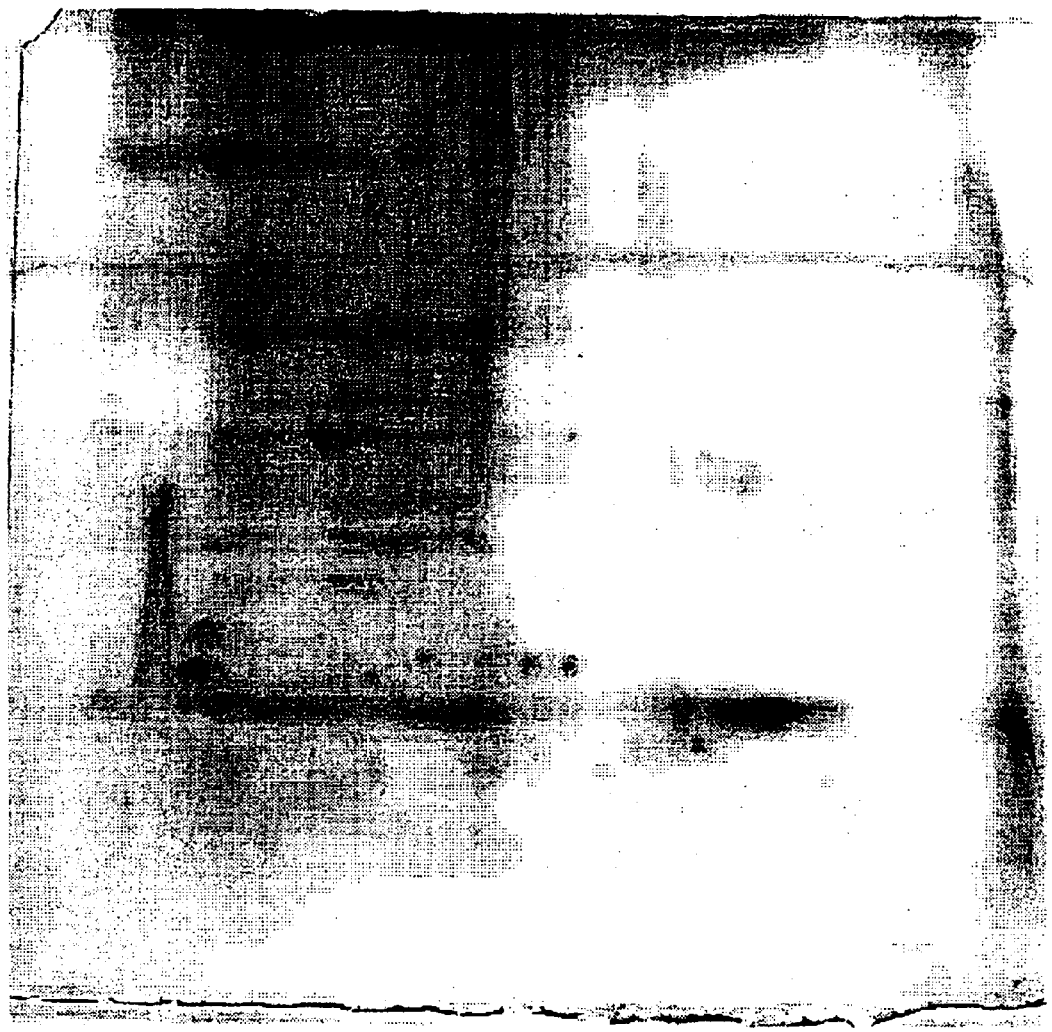
FIG. 6 shows a gel image where the rehydration liquid containing a sample has been loaded passively, ie while not subject to an electric current.

FIG. 6 shows a gel image where the rehydration liquid containing a sample of Human red blood cells has been loaded passively, ie while not subject to an electric current. The sample was prepared according to the method of Beutler, E., West, C., Blume, K-G., *J. Lab. Clin. Med.* 1976, 88, 328–333. The membrane samples were then solubilised in a solution containing 7M urea, 2M thiourea, 1% C7Bz0 (a detergent) and 3 mM tributyl phosphine. The solubilised protein was then loaded (passively) onto the dry IPG strip by rehydration in the case of the example shown in FIG. 6 without active rehydration.

EXAMPLE

Figure 7:
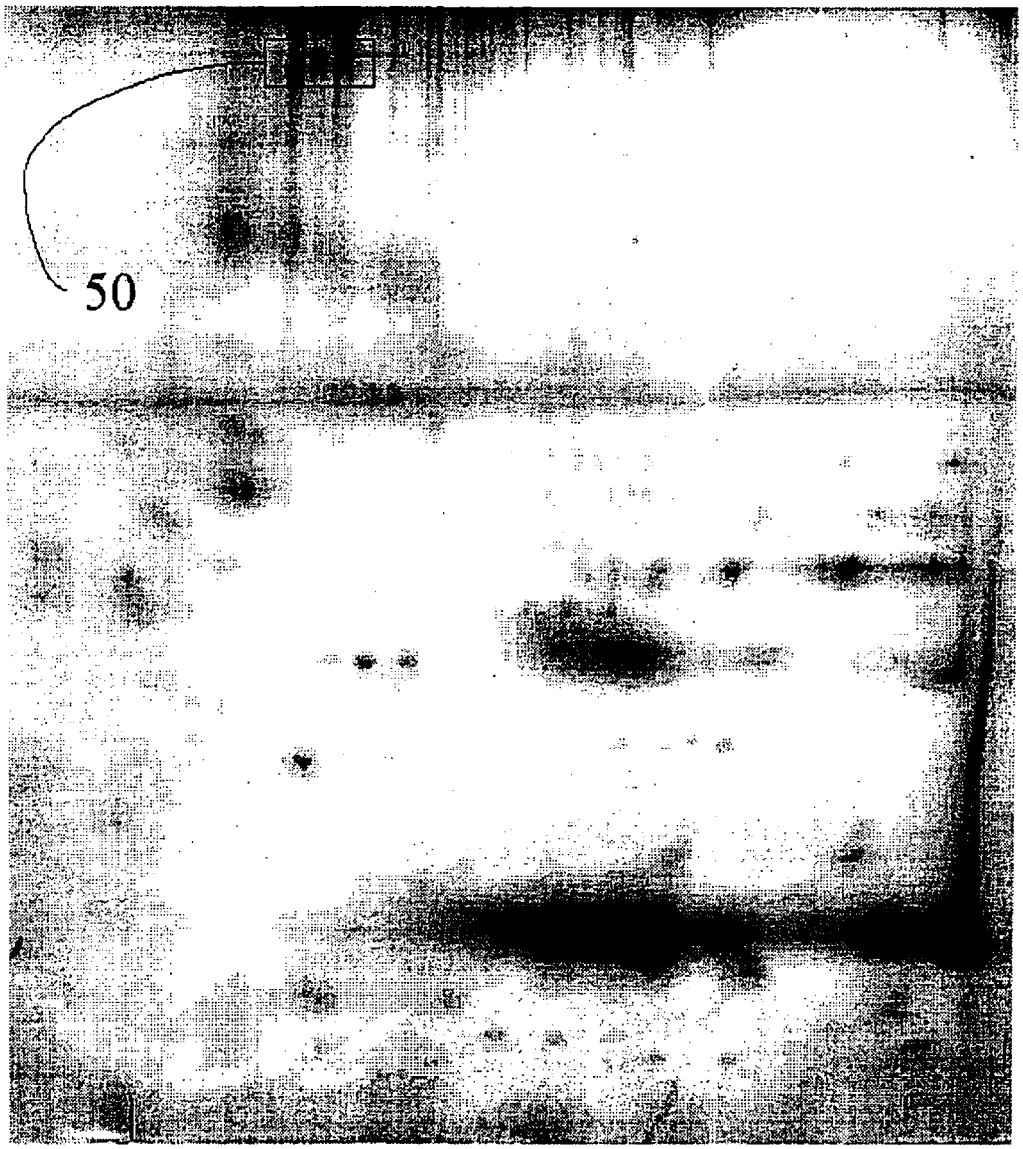
FIG. 7 shows a gel image where the rehydration liquid containing a sample has been loaded actively, while subject to an electric current.

FIG. 7 shows a gel image where the rehydration liquid containing a sample of Human red blood cells prepared according to the example set out above has been loaded actively, while subject to low voltage of about 50 volts. As can be seen in comparison with the gel shown in FIG. 6 the final gel strip shown in FIG. 7 is better than the passively loaded strip because there are more distinct protein spots resolved. Also the large amount of smearing which is apparent in FIG. 6 is not present on FIG. 7. Further high molecular weight proteins are better resolved on the active gel. It is possible to identify "spectrin" (50) a very large 250 kDa prtein on the gel of FIG. 7. Spectrin is a signature protein of RBC membranes and is very difficult to resolve.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An apparatus for rehydrating and for performing electrophoresis on a gel strip including:
   a tray defining a plurality of troughs each configured to receive a gel strip, each trough defining both a centrally located rehydration area and an electrode area disposed at either side of the rehydration area;
   means for delimiting the rehydration area of each trough from the electrode areas; and
   an electrode comprising contact points adapted to contact either the gel strip in the electrode areas near a first and second end of the gel strip or a conducting or current carrying electrode bridge material which is in contact with the gel strip in the electrode areas, the electrode being adapted to be connected to a source of electric current for imposing an electric potential in the gel strip between the electrode areas.

2. An apparatus as claimed in claim 1, wherein the means for delimiting the rehydration area of the troughs from the electrode areas comprises delimiting walls extending laterally across the width of the troughs and an air gap defined between the electrode and the wall adjacent said electrode.

3. An apparatus as claimed in claim 1, wherein the means for delimiting the rehydration area of each trough from one of the electrode areas includes two spaced apart parallel walls which extend across each trough defining a gap there between.

4. An apparatus as claimed in claim 2 wherein a part of the gel strip in the rehydration area of the troughs adjacent the delimiting wall contacts a conducting/current carrying electrode bridge.

5. An apparatus as claimed in claim 4 wherein the conducting/current carrying electrode bridge comprises an absorbent material wetted with an electrically conducting liquid.

6. An apparatus as claimed in claim 5 wherein the absorbent material is paper.

7. An apparatus as claimed in claim 1 wherein the electrode areas are deeper than the rehydration areas.

8. An apparatus as claimed in claim 1, wherein a laterally extending channel is defined in a floor of the troughs.

9. An apparatus as claimed in claim 1, wherein the troughs do not include embedded electrodes and the electrode contacts the electrode bridge material from above.

10. An apparatus as claimed in claim 1, wherein the tray includes a dry IPG gel strip and dry electrode bridge material located in place in the trough.

11. An apparatus as claimed in claim 1 further including pressure applying means which rest on each gel strip where the strips overlap the electrode bridge material to ensure a good electrical contact between the gel strips and the electrode bridge material.

12. An apparatus as claimed in claim 1, wherein the tray defines a plurality of substantially parallel troughs.

13. A method of rehydrating and performing electrophoresis on a gel strip comprising the steps of:
   providing a tray defining at least one trough with a gel strip, located in said trough, the trough defining both a centrally located rehydration area and an electrode area disposed on at least one side of the centrally located rehydration area in which an absorbent electrode bridge is provided;
   wetting the electrode bridge with an electrically conducting liquid;
   adding rehydration liquid, containing a sample to be separated by electrophoresis into the centrally located rehydration area of the trough without contacting the electrode area with the rehydration liquid;
   inserting a dry gel strip into the trough if a gel strip is not already present in the trough, the gel strip being longer than the rehydration area so that its ends rest on the electrode bridge;
   applying relatively low voltage across the gel strip during a first period in which rehydration of the gel strip occurs;
   subsequently applying a relatively higher voltage to perform electrophoresis on the sample.

14. The method of claim 13 wherein the sample is a mixture of macromolecules selected from the group consisting of protein samples containing DNA, RNA, amino acids and other components which can be separated by electrophoresis.

15. An apparatus for performing electrophoresis on a gel strip comprising:
   a tray defining both a rehydration trough that receives rehydration fluid containing macromolecules and an electrode trough, wherein the rehydration trough and the electrode trough are separated from each other so as to inhibit the flow of rehydration fluid from the rehydration trough to the electrode trough;
   a gel strip that is positioned within the rehydration trough;
   an electrode assembly positioned within an electrode area of the electrode trough wherein the electrode assembly provides current which is supplied to the gel strip wherein the electrode assembly is positioned within the electrode area of the electrode trough such that contact of the macromolecules in the rehydration fluid and the electrode assembly is inhibited when the rehydration fluid is positioned within the rehydration trough.

16. The apparatus of claim 15, wherein a wall is interposed between the rehydration trough and the electrode trough of the tray.

17. The apparatus of claim 16, wherein the electrode assembly includes an electrode bridge material positioned within the electrode trough such that an air gap is interposed between the electrode bridge material and the wall interposed between the rehydration trough and the electrode trough of the tray.

18. The apparatus of claim 17, wherein the gel strip is positioned within the rehydration trough such that a portion of the gel strip extends to contact the electrode assembly adjacent the electrode bridge material.

19. The apparatus of claim 18, wherein the electrode assembly further includes an electrode that contacts the electrode bridge material from a position above the electrode bridge material and the floor of the electrode trough.

20. The apparatus of claim 19, wherein the gel strip comprises a dry gel strip that is hydrated by the rehydration fluid and the electrode bridge material initially comprises a dry electrode bridge material that must be hydrated.

21. The apparatus of claim 16, wherein the floor of the rehydration trough includes a laterally extending channel positioned therein.

22. The apparatus of claim 21, wherein the floor of the rehydration trough is flat and includes sloped ends which slope upwards towards the wall interposed between the rehydration trough and the electrode trough.

23. The apparatus of claim 21, wherein the floor of the rehydration channel is curved along the base of its length.

* * * * *